United States Patent [19]

Horrobin et al.

[11] Patent Number: 5,635,189
[45] Date of Patent: Jun. 3, 1997

US005635189A

[54] TOCOPHEROLS

[75] Inventors: David F. Horrobin, Guildford; Mehar S. Manku, Carlisle, both of England

[73] Assignee: Scotia Holdings PLC, England

[21] Appl. No.: 297,215

[22] Filed: Aug. 29, 1994

[30] Foreign Application Priority Data

Sep. 3, 1993 [GB] United Kingdom ............ 9318271

[51] Int. Cl.$^6$ ............................................ A61K 9/14
[52] U.S. Cl. ........................ 424/401; 424/489; 424/490
[58] Field of Search ........................... 424/401, 195.1, 424/489, 490; 514/904, 772.3

[56] References Cited

U.S. PATENT DOCUMENTS

| | | | |
|---|---|---|---|
| 4,977,282 | 12/1990 | Baldwin et al. | 549/412 |
| 4,996,375 | 2/1991 | Barner et al. | 568/853 |
| 5,234,695 | 8/1993 | Hobbs et al. | 424/489 |

FOREIGN PATENT DOCUMENTS

| | | |
|---|---|---|
| 0 171 009 A2 | 2/1986 | European Pat. Off. |
| 0 421 419 A3 | 4/1991 | European Pat. Off. |
| 1360759 | 3/1963 | France . |
| 2 602 772 | 2/1988 | France . |

OTHER PUBLICATIONS

Chemical Abstract, vol. 94 No. 13, 1981 abstract No. 103165c p. 724 JP–A–8 081 879.

Chemical Abstracts, vol. 105, No. 30, 1986 abstract No. 134192j p. 703 JP–A–60 149 582.

Chemical Abstracts vol. 108, No. 17 1988 abstract No. 203390y p. 565.

*Primary Examiner*—Thurman K. Page
*Assistant Examiner*—Sharon Howard
*Attorney, Agent, or Firm*—Nixon & Vanderhye

[57] ABSTRACT

A natural vitamin E preparation, i.e. vitamin E extracted from natural sources, comprising one or more of the alpha-, beta-, gamma- and delta-tocopherol forms, either as the tocopherol itself, or as a derivative, such as the acetate, in which the total concentration of Wendt PAHs is less than 100 ppb.

11 Claims, No Drawings

TOCOPHEROLS

Polycyclic aromatic hydrocarbons (PAHs) are a group of compounds which are near ubiquitous in the environment. Some of these compounds are carcinogenic. They are produced in the course of many different types of industrial activity and are present in substantial amounts in the atmosphere. They are picked up by plants from the atmosphere and so, paradoxically, some of the foods which are regarded as healthy are the most contaminated.

Wendt described the major PAHs likely to be present in foodstuffs and identified in particular 6 "light" and 7 "heavy" PAHs (see Table 1). The heavy PAHs are the ones which are most likely to be toxic.

We produce vegetable oils and are concerned to ensure that PAH levels in products for sale are kept well within appropriate levels. Recently what is regarded as an unacceptable level of PAHs was found in a finished product to which had been added natural vitamin E. The PAH levels in the oil itself were well within acceptable limits. After a great deal of investigation of all possible sources of PAH contamination it was concluded that the excess PAH had been added in the natural vitamin E. This was surprising, since we had not previously known of any reports of PAH contamination of vitamin E. However, natural vitamin E comes from plant sources, usually soya or wheat, and is prepared by a series of concentration steps which could well concentrate the PAHs as well as the vitamin E.

There are three major manufacturers of natural vitamin E in the world, and samples were obtained from all three. The samples were analysed for the 13 PAHs in the Wendt classification. The results are shown in Table 1 below. The Table sets out the 13 PAHs identified by Wendt as possible important contaminants of foods and their levels in commercial samples of d-alpha-tocopherol acetate supplied by three manufacturers. All figures are in ppb.

TABLE 1

| | Supplier A | Supplier B | Supplier C |
|---|---|---|---|
| Light PAHs | | | |
| Phenanthrene | 27 | <1 | <2 |
| Anthracene | 4 | 59 | 125 |
| Fluoranthene | 4 | 106 | 34 |
| Pyrene | 4 | 3244 | 2018 |
| Benzo(a)anthracene | 2 | 9 | 42 |
| Chrysene + triphenylene | 10 | 191 | 2328 |
| Heavy PAHs | | | |
| Benzo(a)pyrene | 28 | 30 | 106 |
| Benzo(e)pyrene | 285 | 2 | 521 |
| Perylene | 35 | 2 | 289 |
| Anthanthrene | 10 | <1 | 4 |
| Benzo(g,h,i)perylene | 81 | 2 | 90 |
| Dibenzo(a,h)anthracene | 5 | <1 | <1 |
| Coronene | 1 | <1 | 2 |
| Total | 526 | 3646 | 5560 |

As can be seen from Table 1, while the samples vary, they all contain unacceptably high levels of one or more PAHs. Thus natural vitamin E preparations, either used by themselves or added to other foods or food supplements, could prove to be significant sources of human PAH intake.

The final end use of the vitamin E is clearly relevant in the determination of satisfactory PAH levels. The invention provides a natural vitamin E preparation comprising one or more of the alpha-, beta-, gamma- and delta-tocopherol forms, either as the tocopherol itself, or as a derivative, such as acetate, in which the total concentration of Wendt PAHs is less than 100 ppb. The PAH concentration in the preparation is further suitably less than 60 µg/kg (ppb), more suitably less than 30 µg/kg (ppb), preferably less than 15 µg/kg (ppb), more preferably less than 5 µg/kg (ppb) and most preferably less than 1 µg/kg (ppb). Obviously the more natural vitamin E is incorporated in any end use, the lower should be the permitted concentration.

The vitamin E preparation may be used by itself as a nutritional supplement or as an agent to be added to other foods, food additives, nutritional supplements, pharmaceuticals, skin care products or products of any other type for human or veterinary use. Ordinarily the required PAH levels will be reached by purification, but we do not exclude the case when the vitamin E is from sources selected so as to have acceptable PAH levels, naturally or by control of the growing environment.

Various techniques are suitable for the removal of PAHs from natural lipids. In general, the following techniques may all be used to produce oils and vitamin E preparations with satisfactory PAH levels. These methods include but are not limited to the following:

1. Liquid/liquid extraction, using for example mixer-settlers, countercurrent extractors, centrifugal extractors or columns. The principle is to mix the tocopherols with a light non-polar solvent such as cyclohexane, hexane or other appropriate hydrocarbon. This mixture is then mixed with any appropriate polar solvent such as dimethylformamide (DMF)/water, or sulpholane/water. The PAHs are extracted into the polar solvent fraction which is then separated from the tocopherol fraction by standard industrial techniques and, if appropriate, further purification can be achieved by passing through a silica gel column.

2. High pressure liquid chromatography (HPLC) using any appropriate commercially available system can be used. Typical column packings for straight phase are LiChrosorb Si 60 or equivalent, or for reverse phase separation a C18 column with 30–40µ packing. For normal phase operation an appropriate isocratic condition solvent is iso-octane:isopropanol 99.5:0.5 v/v or equivalent. For reverse phase operation with the tocopherol material dissolved in a solvent such as acetone, a suitable solvent system is methanol:water, 99.5:0.5 v/v or equivalent.

3. Flash chromatography using a nitrogen or other appropriate gas driven column. As an example, a glass column can be packed with Silica Gel 60, a prefilter containing charcoal such as Norit SA4 and a filter such as celite. The contaminated tocopherols are dissolved in hexane at, for example, a 1:2 ratio and become separated when passing through the column and are collected. The solvent is then removed to produce the purified tocopherols. Alternatively, ultrapurification of tocopherols can be achieved by flash chromatography using a C18 type packing.

4. Methods using formation of complexes between caffeine and PAHs with separation of the non-complexed tocopherols.

5. Supercritical fluid extraction followed by preparative or flash column chromatography.

6. Treatment of natural tocopherol mixtures with sulphuric acid or like agent followed by extraction with hexane or other appropriate solvent and final purification by flash chromatography.

Examples of methods for reducing the PAH levels in vitamin E

A. Liquid-liquid extraction methods

There are several ways of doing this, some of which are set out below:

1. Mix the tocopherol (TP) with 10 times the volume of cyclohexane, pestiscan grade. Add to this an approximately equal volume of a 90:10 mixture of dimethylformamide:water and mix thoroughly for about 2 minutes. Allow the mixtures to settle and separate. The lower aqueous phase containing the PAHs is then removed. The upper cyclohexane layer containing the TP is then washed again in the same way with a dimethylformamide:water mixture. The upper cyclohexane layer is then collected and evaporated in a rotary evaporator under high vacuum to distill off the cyclohexane leaving behind the PAH-free TP.

2. Mix the TP with 10 times the volume of cyclohexane, pestiscan grade. Add an approximately equal volume of a 90:10 sulfolane:water mixture and mix thoroughly for about 3 minutes. Allow the mixtures to settle and separate and remove the lower aqueous layer containing the PAHs. Wash the upper cyclohexane layer again with the sulfolane:water mixture. Collect the upper cyclohexane layer and evaporate under high vacuum in a rotary evaporator. The material left after solvent removal is the PAH-free TP.

B. Slurry technique

Prepare a Celite filter pad in a funnel of appropriate size using Celite 521 filter agent (BN374020114 from Fisons) or a similar material. Add 0.5% by weight of charcoal (such as Norit SA4) to the TP. Mix the TP and charcoal well and filter the slurry through the Celite filter using a vacuum. The filtrate is the PAH-free TP.

C. Column chromatography

This can be done using a number of different columns, solid phases and solvents. For example, a column can be loaded with silica gel 60 (6 length units), charcoal (Norit SA4) (7 length units) and Celite 521 (2 length units). The TP is mixed with about twice its volume of HPLC grade hexane and applied to the column under nitrogen pressure. The column is then eluted with more hexane and the eluent collected. The hexane is then evaporated under vacuum leaving behind the PAH-free TP.

D. Caffeine-formic acid complexation

TP is dissolved in about five times the volume of cyclohexane, pestiscan grade. A volume of formic acid/ caffeine solution equal to the original volume of TP is then added and mixed. The formic acid/caffeine solution is made by diluting 9 parts of 98–99% formic acid with 1 part of HPLC grade water, in which is dissolved 15% by weight of caffeine.

After mixing the lower formic acid/caffeine layer was discarded and the cyclohexane layer washed again with a further quantity of formic acid/caffeine. The cyclohexane layer was collected and evaporated under high vacuum to remove excess solvent, leaving behing the PAH-free TP.

Results of tests to reduced PAHs in commercial vitamin E samples

A commercial sample of vitamin E was tested for the presence of the Wendt PAHs. The six light PAHs are not considered to be harmful to health in any important way: they are phenanthrene, anthracene, fluoroanthrene, pyrene, benzo(a)anthracene, chrysene and triphenylene. The seven heavy PAHs on the other hand are regarded as potentially dangerous, particularly with regard to carcinogenicity. They are: benzo(e)pyrene, benzo(a)pyrene, perylene, DiB(a,h) anthracene, benzo(ghi)perylene, anthanthrene and coronene.

Natural vitamin E was purchased from a commercial supplier and analysed for the light and heavy PAHs. The sum of the light PAHs in the sample was 25.7 microg/kg whereas the sum of the heavy PAHs was 299.4 microg/g.

The natural vitamin E was then subjected to treatment by four of the five methods set out in the examples. The levels of PAHs in the vitamin E after treatment are shown below:

| Treatment | Heavy PAHs | Light PAHs |
| --- | --- | --- |
| Cyclohexane/dimethylf. | 12.8 | 6.3 |
| Cyclohexane/sulfolane | 5.6 | 11.3 |
| Column chromatography | 16.8 | 10.5 |
| Caffeine/formic acid | 30.4 | 14.4 |

All figures are in microg/g.

It can be seen that all the techniques produced a very substantial reduction in the PAH levels. This is particularly evident for the heavy PAHs which are brought down to values which are regarded as safe for human consumption. The light PAHs, which are not regarded as dangerous, are also substantially reduced.

We claim:

1. A preparation comprising vitamin E extracted from natural sources, wherein the vitamin E is present as one or more of the alpha-, beta-, gamma- or delta-tocopherol forms, either as the tocopherol itself, or in a pharmacologically, nutritionally or cosmetically acceptable form, and wherein the total concentration of Wendt polycyclic aromatic hydrocarbons (PAHs) is less than 100 ppb.

2. A preparation according to claim 1, wherein the total concentration is less than 60 ppb.

3. A preparation according to claim 2, wherein the total concentration is less than 30 ppb.

4. A preparation according to claim 3, wherein the total concentration is less than 15 ppb.

5. A preparation according to claim 4 wherein the total concentration is less than 5 ppb.

6. A preparation according to claim 5, wherein the total concentration is less than 1 ppb.

7. A natural vitamin E preparation according to claim 1, wherein the PAH concentration has been reached by purification of the vitamin E with selective removal of PAH.

8. A nutritional supplement or food additive comprising a vitamin E preparation extracted from natural sources, wherein the vitamin E is present as one or more of the alpha-, beta-, gamma- or delta-tocopherol forms, either as the tocopherol itself, or in a nutritionally acceptable form, and wherein the total concentration of Wendt PAHs is less than 100 ppb.

9. A pharmaceutical composition comprising a vitamin E preparation extracted from natural sources, wherein the vitamin E is present as one or more of the alpha-, beta, gamma- or delta-tocopherol forms, either as the tocopherol itself, or in a pharmacologically acceptable form, and wherein the total concentration of Wendt PAHs is less than 100 ppb.

10. A skin care product comprising a vitamin E preparation extracted from natural sources, wherein the vitamin E is present as one or more of the alpha-, beta-, gamma- or delta-tocopherol forms, either as the tocopherol itself, or in a cosmetically acceptable form, and wherein the total concentration of Wendt PAHs is less than 100 ppb.

11. A process of reducing the PAH levels in vitamin E comprising treating a composition comprising vitamin E extracted from natural sources, wherein the vitamin E is present as one or more of the alpha, beta-, gamma-, or delta-tocopherol by liquid/liquid extraction, high pressure liquid chromatography, flash chromatography, complex formation, supercritical fluid extraction or combinations thereof to reduce the PHAs level to a total concentration of Wendt PAHs to less than 100 ppb.

* * * * *